(12) United States Patent
Nara

(10) Patent No.: US 9,687,149 B2
(45) Date of Patent: Jun. 27, 2017

(54) SLIT LAMP MICROSCOPE

(71) Applicant: Takagi Seiko Co., Ltd., Nakano-shi, Nagano (JP)

(72) Inventor: Takeshi Nara, Nakano (JP)

(73) Assignee: TAKAGI SEIKO CO., LTD., Nakano-Shi, Magano (JP)

( * ) Notice: Subject to any disclaimer, the term of this patent is extended or adjusted under 35 U.S.C. 154(b) by 0 days.

(21) Appl. No.: 14/863,966

(22) Filed: Sep. 24, 2015

(65) Prior Publication Data
US 2016/0095516 A1    Apr. 7, 2016

(30) Foreign Application Priority Data
Oct. 1, 2014  (JP) .................. 2014-203152

(51) Int. Cl.
*A61B 3/135*    (2006.01)
*A61B 3/00*     (2006.01)
*A61B 3/15*     (2006.01)

(52) U.S. Cl.
CPC ........... *A61B 3/135* (2013.01); *A61B 3/0083* (2013.01); *A61B 3/156* (2013.01)

(58) Field of Classification Search
CPC .................................................. A61B 3/135
USPC ............... 351/214, 206, 246, 221, 205, 200
See application file for complete search history.

(56) References Cited

U.S. PATENT DOCUMENTS

| 7,147,328 B2 * | 12/2006 | Sugino ............... A61B 3/14 351/200 |
| 2014/0211163 A1 * | 7/2014 | Maruyama ........ A61B 3/135 351/214 |

FOREIGN PATENT DOCUMENTS

| JP | 2011-177273 A | 9/2011 |
| JP | 2014-33812 A | 2/2014 |

* cited by examiner

*Primary Examiner* — Hung Dang
(74) *Attorney, Agent, or Firm* — Birch, Stewart, Kolasch & Birch, LLP

(57) ABSTRACT

The slit lamp microscope comprises: a supporting base capable of precisely horizontally moving with respect to a frame; a supporting section extended upward from the supporting base; a slit light unit attached to a front end part of the supporting section, the slit light unit accommodating a slit lamp which emits a slit light downward; a mirror unit attached to a vertical middle part of the supporting section, the mirror unit having a reflecting mirror, which reflects the slit light from the slit light unit toward an eye of an examinee; and a microscope unit for observing the eye of the examinee. A slit lamp power cable, which supplies electric power to the slit lamp and which is extended from the supporting base, is provided in a hollow part of the supporting section and connected to the slit lamp in the slit light unit without being exposed outside.

4 Claims, 6 Drawing Sheets

SLIT LAMP MICROSCOPE

CROSS-REFERENCE TO RELATED APPLICATION

This application is based upon and claims the benefit of priority of the prior Japanese Patent Application No. P2014-203152, filed on Oct. 1, 2014, and the entire contents of which are incorporated herein by reference.

FIELD

The present invention relates to a slit lamp microscope for observing an eye of an examinee with a slit lamp.

BACKGROUND

A slit lamp microscope is used, by an ophthalmologist, for observing an eye (an anterior eye part) of an examinee.

A conventional slit lamp microscope will be explained.

The slit lamp microscope irradiates an eye of an examinee with a slit light from an oblique direction so as to visualize and observe transparent or semi-transparent tissues. The slit lamp microscope includes a slit light optical system for emitting the slit light and a microscope unit.

Generally, a slit light source is provided above a mirror. The slit light emitted downward from the light source is reflected, by the mirror, to irradiate the eye of the examinee.

Therefore, a cable for supplying electric power to the light source is usually connected to an upper end part of the slit light optical system (see FIG. 1 of Patent Document 1).

In case of irradiating the eye of the examinee with the slit light only, an irradiation point on the eye is sometimes unknown. In this state, if a picture of the eye is taken, the slit light will be focused on a slit. To solve this problem, a backlight source for illuminating a circumference of the slit light, is provided to the conventional slit lamp microscope.

Patent Document 2 discloses light emitting diodes (LEDs) used as a backlight source. An auxiliary lamp unit including the LEDs is attached to a front end part of a flexible arm.

The flexible arm is attached to a face supporting section, which supports a face of the examinee, and the backlight is emitted from a position above the eye of the examinee.

PRIOR ART DOCUMENTS

Patent Documents

Patent Document 1: Japanese Laid-open Patent Document No. 2014-33812

Patent Document 2: Japanese Laid-open Patent Document No. 2011-177273

SUMMARY

In the conventional slit lamp microscope disclosed in Patent Document 1, a cable of the slit light source is connected to the upper end part of the slit light optical system from a position under the slit lamp microscope, so the exposed cable is unsightly for both of the examinee and an observer (e.g., an ophthalmologist).

In case of the slit lamp microscope for examining eyes, there is a possibility that the eye observation is interfered by the unsightly cable.

Accordingly, it is an object to provide a slit lamp microscope, in which no unsightly cables are disposed outside and which is capable of correctly observing eyes.

To achieve the object, the present invention has following structures.

Namely, the slit lamp microscope of the present invention comprises:

a frame;

a supporting base being capable of precisely moving, in a horizontal direction, with respect to the frame;

a supporting section being extended upward from the supporting base;

a slit light unit being attached to a front end part of the supporting section, the slit light unit accommodating a slit lamp which emits a slit light downward;

a mirror unit being attached to a vertical middle part of the supporting section, the mirror unit having a reflecting mirror, which reflects the slit light emitted from the slit light unit toward an eye of an examinee; and a microscope unit for observing the eye of the examinee, and a slit lamp power cable, which supplies electric power to the slit lamp and which is extended from the supporting base, is provided in a hollow part of the supporting section and connected to the slit lamp in the slit light unit without being exposed outside.

With this structure, no slit lamp power cable is disposed outside of the slit lamp microscope, so that correct observation of eyes can be performed without being interfered with the unsightly cable.

In the slit lamp microscope, a backlight source for emitting a backlight, which illuminates a circumference of the slit light toward the eye of the examinee, may be provided to the mirror unit, and a backlight power cable, which supplies electric power to the backlight source and which is extended from the supporting base, may be provided in the hollow part formed in the supporting section and connected to the backlight source in the mirror unit without being exposed outside.

With this structure, no backlight power cable is disposed outside of the slit lamp microscope, so that correct observation of eyes can be performed without being interfered with the unsightly cable.

In the slit lamp microscope, the supporting base may be disposed such that a clearance is formed between a lower face of the supporting base and an upper face of the frame, a conversion circuit, which converts a commercial electric power source or an electric power source from an AC adapter into a driving power source of the slit lamp and the backlight source, may be provided in the inside of the supporting base, and an opening part, into which an electric power cable from the commercial electric power source or the AC adapter is introduced so as to be connected to the conversion circuit, may be formed in the lower face of the supporting base.

With this structure, no electric power cable extended from the commercial electric power source or the AC adapter is disposed on the supporting base, so that correct observation of eyes can be performed without being interfered with the unsightly cable.

In the present invention, the slit lamp microscope has the built-in cable or cables, so that correct observation of eyes can be performed without being interfered with the unsightly cable or cables.

BRIEF DESCRIPTION OF THE DRAWINGS

Embodiments of the present invention will now be described by way of examples and with reference to the accompanying drawings, in which.

DETAILED DESCRIPTION OF THE EMBODIMENTS

Preferred embodiments of the present invention will now be described in detail with reference to the accompanying drawings.

Figure 1:
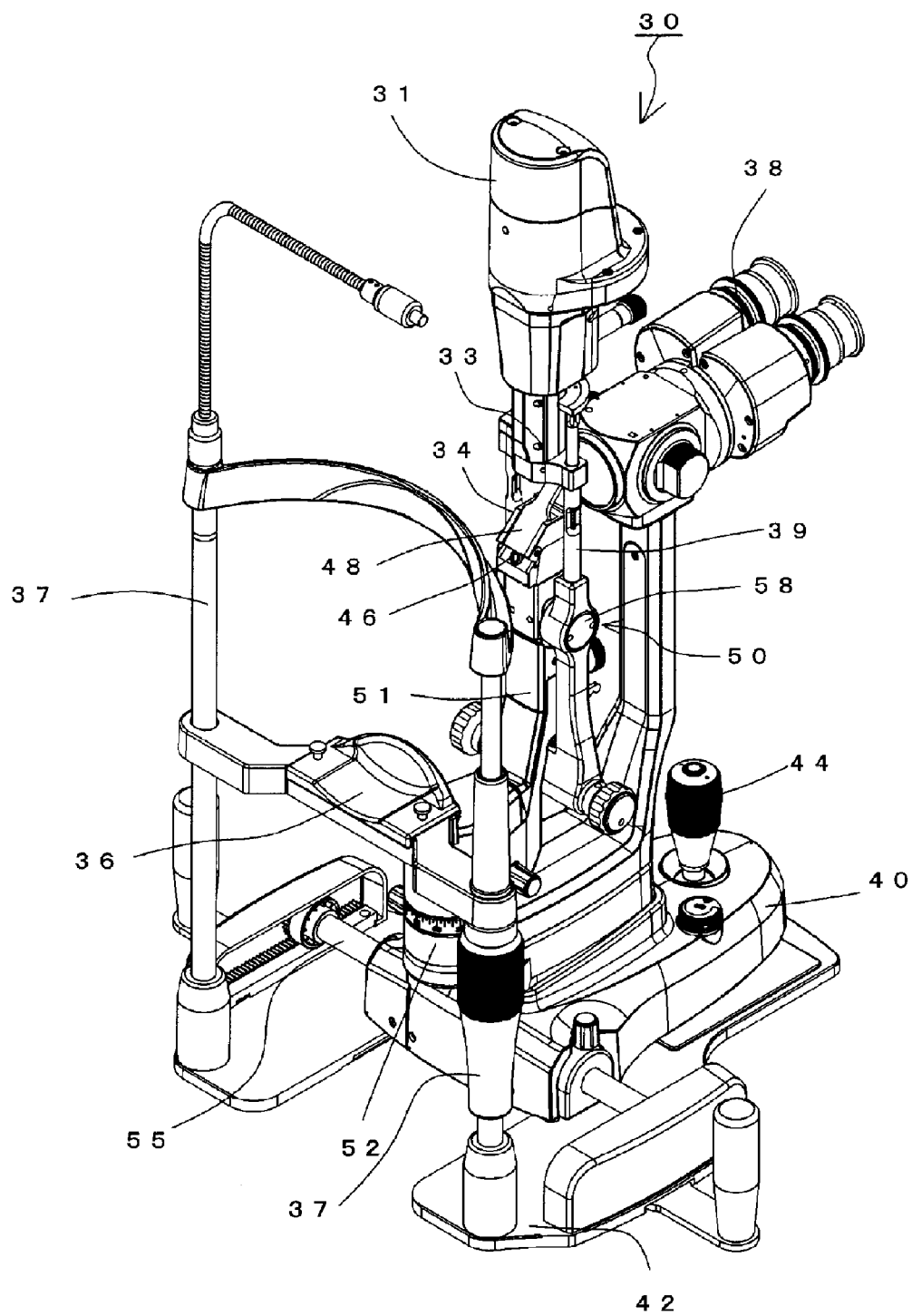
FIG. 1 is a perspective view of a slit lamp microscope of an embodiment of the present invention.

A whole structure of a slit lamp microscope 30 of the present embodiment is shown in FIG. 1.

The slit lamp microscope 30 comprises: a slit light unit 31, which has a built-in slit lamp 32 for emitting a slit light (see FIGS. 3 and 4); and a mirror unit 34 for reflecting a slit light emitted from the slit lamp 32 toward an eye of an examinee.

In the present embodiment, the slit light unit 31 emits the slit light downward, and the mirror unit 34 is provided under the slit light unit 31.

Note that, the slit light unit 31 may be provided under the mirror unit 34, and the slit light emitted upward may be reflected, by the mirror unit 34, toward the eye of the examinee.

The slit light unit 31 and the mirror unit 34 are connected to each other by two connection pillar 39, which constitute a supporting section 50. The mirror unit 34 is disposed between the two connection pillar 39, and the slit light unit 31 is spanned between upper ends of the two connection pillar 39. A slit light emitting port 33 of the slit lamp unit 31 is disposed between the two connection pillar 39.

Figure 2:
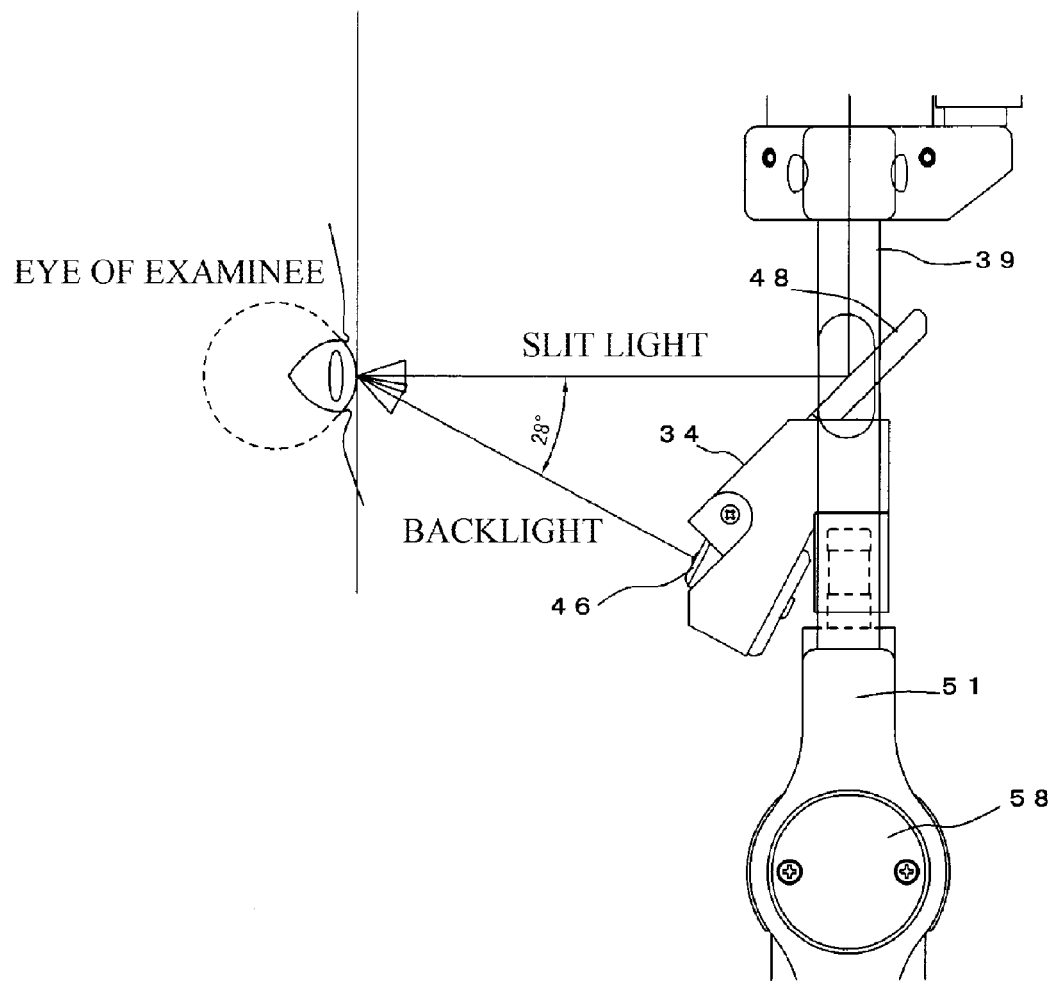
FIG. 2 is a side view of a mirror unit.

A manner for emitting the slit light and a backlight toward the eye of the examinee will be briefly explained with reference to FIG. 2.

In the present embodiment, a backlight source 46, which emits the backlight for illuminating a circumference of the slit light, is integrated with the mirror unit 34. The backlight source 46 emits the backlight toward the eye of the examinee as well as the slit light.

The mirror unit 34 has a reflecting mirror 48 which is set to face the eye of the examinee. The reflecting mirror 48 is inclined 45 degrees with respect to a light path of the slit light, which is emitted in the vertical direction from the slit lamp 32, so as to irradiate the eye of the examinee with the slit light.

In the present embodiment, the backlight source 46 is provided under the reflecting mirror 48. The backlight source 46 emits the backlight, toward the eye, from a position under a horizontal plane including the eye. A light path of the backlight is inclined 28 degrees with respect to the horizontal plane including the eye, and the backlight is emitted toward the eye of the examinee from underneath.

By emitting the backlight toward the eye of the examinee from the lower position at such angle, glare of the backlight given to the examinee can be reduced.

A chin supporting section 36, on which a chin of the examinee will be mounted, is provided to the slit lamp microscope 30. The chin supporting section 36 is provided between two supporting pillar 37, which are extended in the vertical direction. Lower ends of the supporting pillar 37 are attached to a frame 42.

A microscope 38, which is used for observing an eye of the examinee whose chin has been mounted on the chin supporting section 36, is located to face the chin supporting section 36. Note that, an imaging unit, e.g., camera, may be attached to the microscope 38.

The slit lamp microscope of the present embodiment is characterized in that a slit lamp power cable 66 for supplying electric power to the slit lamp 32 and a backlight power cable 68 for supplying electric power to the backlight source 46 are accommodated in the supporting section 50 without being exposed outside.

Figure 3:
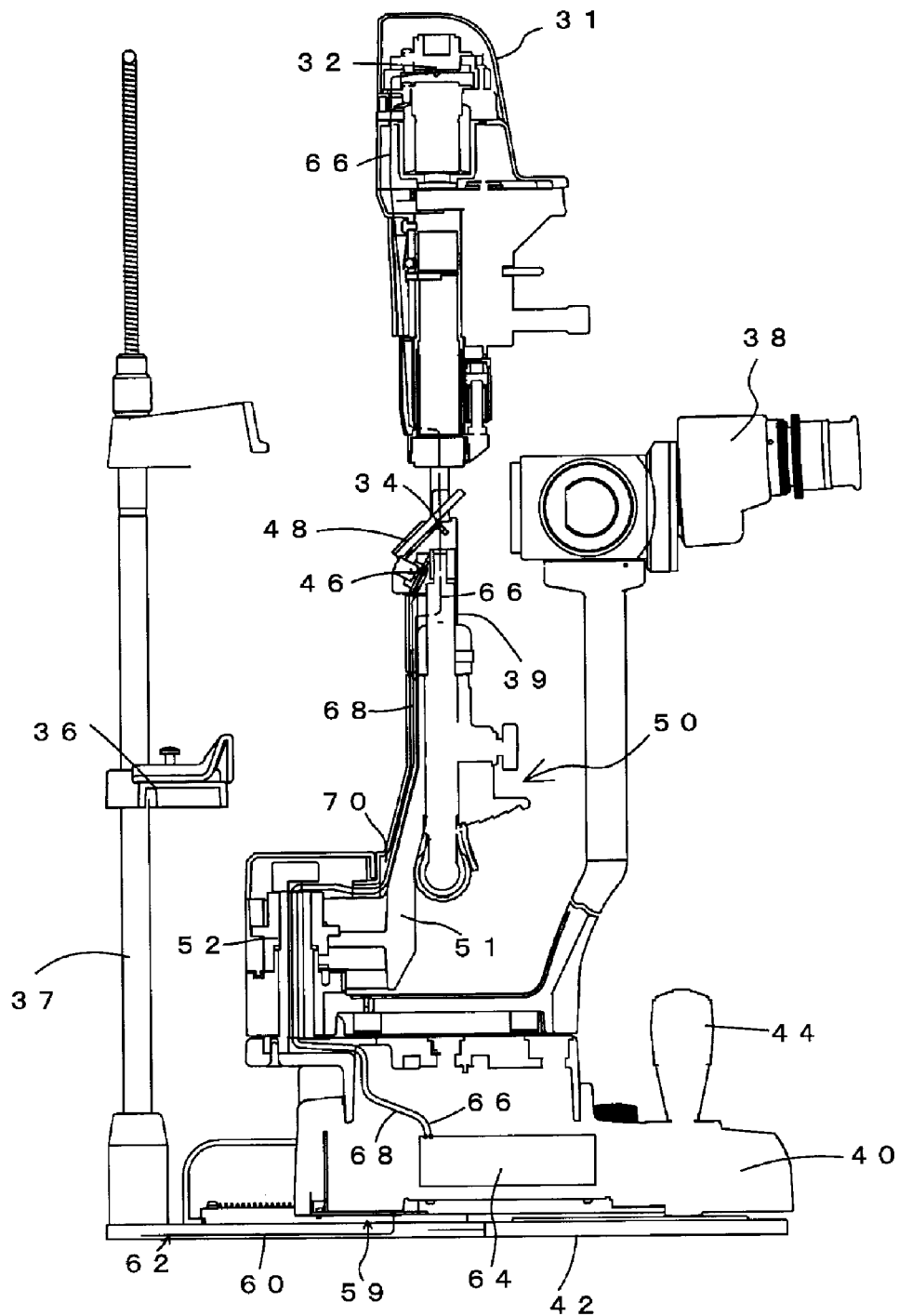
FIG. 3 is a side sectional view of the slit lamp microscope.
Figure 4:
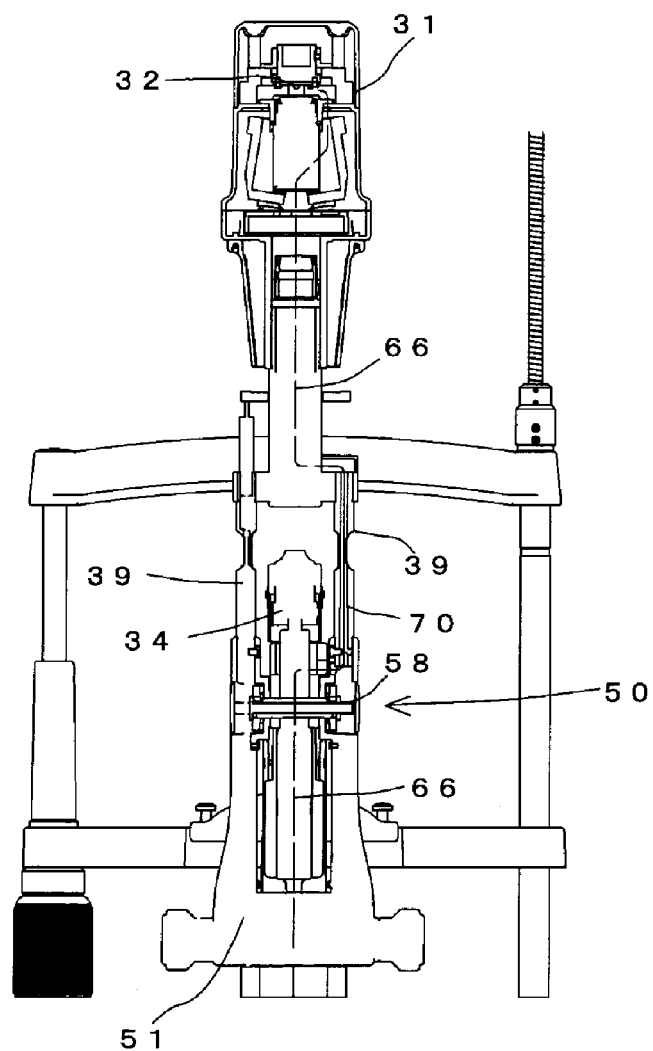
FIG. 4 is a front sectional view of the slit lamp microscope.
Figure 5:
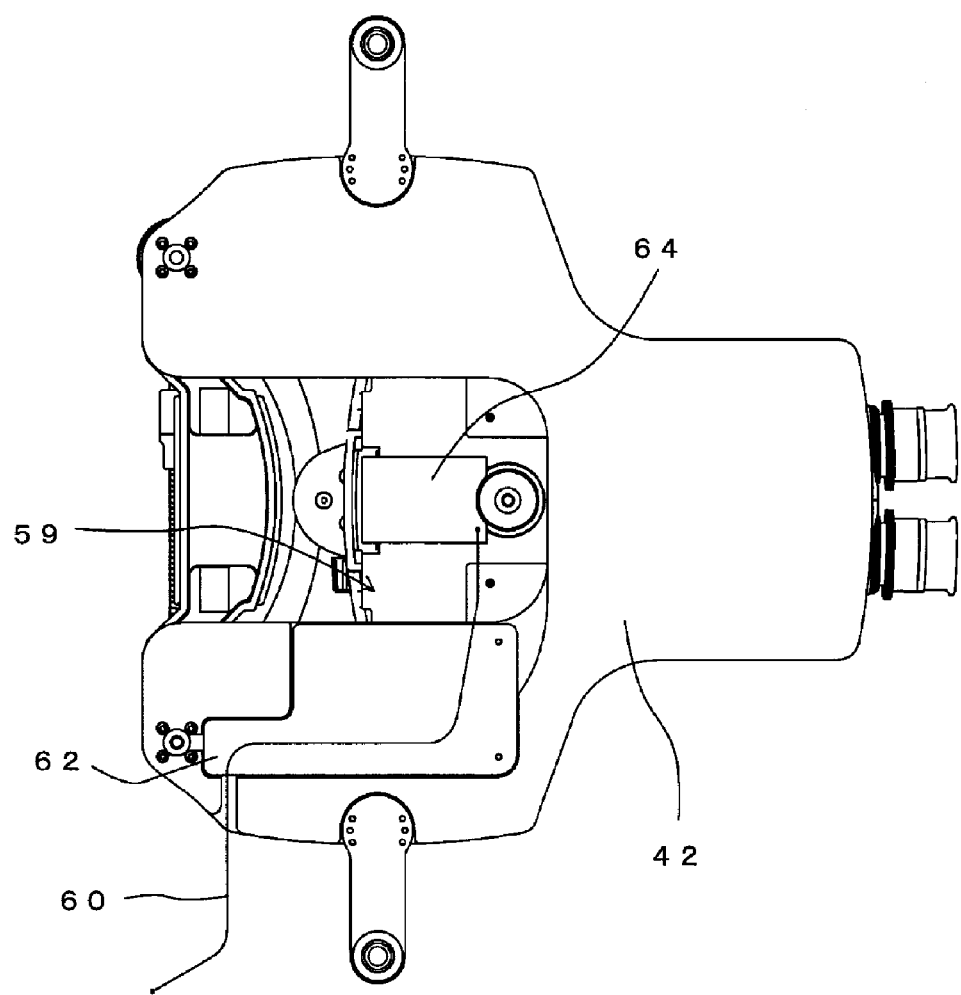
FIG. 5 is a bottom view of the slit lamp microscope.

This characteristic point will be explained with reference to FIGS. 3-5.

A supporting base 40 is capable of precisely moving, with respect to the frame 42, in a horizontal plane. Concretely, the supporting base 40 is attached to a moving shaft 55, which is provided to the frame 42 and arranged in a right-left direction and which is capable of moving in a forth and back direction (i.e., moving close to and away from the examinee). Further, the supporting base 40 is capable of moving in an axial direction of the moving shaft 55. The supporting base 40 can be precisely moved, with respect to the frame 42, in a horizontal plane. The supporting base 40 is precisely moved by operating a joystick 44.

To precisely move the supporting base 40 with respect to the frame 42, a prescribed clearance is formed between a lower face of the supporting base 40 and an upper face of the frame 42.

The slit light unit 31, which is supported by the supporting section 50, and the mirror unit 34 are attached to the supporting base 40. The microscope 38 is also attached to the supporting base 40. Therefore, the slit light unit 31, the mirror unit 34 and the microscope 38 can be simultaneously precisely moved with the precise movement of the supporting base 40.

On the other hand, the supporting pillar 37, to which the chin supporting section 36 is attached, are fixed to the frame 42. Therefore, an irradiation position of the eye to be examined, to which the slit light will be emitted, can be precisely adjusted by precisely moving the supporting base 40.

A groove section 62, in which an electric power cable 60 wired from outside of the slit lamp microscope can be accommodated, is formed in a bottom face of the frame 42. The electric power cable 60 accommodated in the groove section 62 is introduced into an opening part 59 formed in the lower face of the supporting base 40.

Note that, the electric power cable 60 is extended from the commercial electric source of AC 100V.

A conversion circuit 64, which converts the commercial electric power source of AC 100V into driving power sources of the light sources, is provided in the inside of the supporting base 40. Namely, the AC 100V is converted into the driving power sources of the slit lamp 32 and the backlight source 46 by the conversion circuit 64.

The slit lamp power cable 66 for supplying electric power to the slit lamp 32 and the backlight power cable 68 for supplying electric power to the backlight source 46 are extended from the conversion circuit 64.

Note that, the electric power cable 60 for supplying electric power to the slit lamp microscope may be a cable which is connected to an AC adapter (not shown) so as to supply DC electric power. In this case, the conversion circuit 64 is a light control circuit of LEDs.

Note that, the supporting section 50 comprises: a connecting section 51 whose lower end is attached to the supporting base 40; and the two connection pillar 39 which are rotatably attached to the connecting section 51. The lower end of the connecting section 51 is attached to the upper face of the supporting base 40, by a rotary shaft 52 extending in the vertical direction, such that the lower end of the connecting section 51 can be rotated in a horizontal plane.

The mirror unit 34 is provided to an upper end part of the connecting section 51. The two connection pillar 39 are rotatably attached to a side face of the connecting section 51, at positions under the mirror unit 34.

An inclination angle of the connection pillar 39 with respect to the examinee can be changed by a horizontal rotary shaft 58.

The slit lamp power cable 66 and the backlight power cable 68 are wired through a hollow part 70 formed in the supporting section 50 and respectively connected to the slit lamp 32 and the backlight source 46. In the connecting section 51 located at a lower end of the supporting section 50, the rotary shaft 58 is an axially hollow shaft, and the slit lamp power cable 66 and the backlight power cable 68 are disposed in the hollow part of the rotary shaft 58. By passing the slit lamp power cable 66 and the backlight power cable 68 through the inside of the rotary shaft 58, even if the connecting section 51 is rotated about the rotary shaft 58, exerting bad influences on the cables 66 and 68, which are caused by the rotation, can be prevented.

The mirror unit 34 is provided to the upper end part of the connecting section 51, and the hollow part 70, through which the cables pass, is communicated to an inner space of the mirror unit 34. With this structure, the backlight power cable 68 can be introduced into the inner space of the mirror unit 34, without being wired outside of the connecting section 51 from the hollow part 70, and connected to the backlight source 46. Preferably, the backlight source 46 is constituted by LEDs.

The slit lamp power cable 66 is introduced into one of the two connection pillar 39 from the connecting section 51. The slit lamp power cable 66 is wired from the connecting section 51 to the connection pillar 39 via a space formed above the rotary shaft 58.

The hollow part 70 is formed in the one of the connection pillar 39, and the slit lamp power cable 66 extended from the connecting section 50 is accommodated in the hollow part 70.

The hollow part 70 is communicated to an inner space of the slit light unit 31. With this structure, the slit lamp power cable 66 can be introduced into a lower part of the slit light unit 31 from the upper end of the connection pillar 39, without being wired outside, and connected to the slit lamp 32 provided in the slit light unit 31.

Note that, in the above described embodiment, the reflecting mirror 48 is provided in the mirror unit 34.

However, a prism for irradiating the slit light toward the eye of the examinee may be employed instead of the reflecting mirror 48.

Successively, another embodiment, in which a prism is used, will be explained with reference to FIG. 6. Note that, in FIG. 6, the chin supporting section, the supporting arm for supporting the chin supporting section, the microscope and the frame are omitted.

Further, the elements explained in the above described embodiment are assigned the same symbols, and explanation will be omitted.

In the slit lamp microscope 30 of the present embodiment, the slit lamp (not shown) is provided in the supporting base 40. The slit light is emitted upward from a slit light unit.

A cylindrical supporting section 82 is extended upward from the supporting base 40. A light path 84, through which the slit light passes, is formed in the supporting section 82, and a plurality of lenses 86 are provided to a middle part of the light path 84.

A mirror unit 87 including a prism 88 is provided to an upper part of the cylindrical supporting section 82. The prism 88 reflects the slit light, which is emitted from downward, in a horizontal direction.

A backlight source 90 is provided above the prism 88 of the mirror unit 87. Concretely, the backlight source 90 is constituted by LEDs. The backlight source 90 emits the backlight, from obliquely above with respect to a horizontal plane, toward the eye of the examinee.

A backlight power cable 68 for supplying electric power is connected to the backlight source 90. The backlight power cable 68 is provided in the supporting base 40 and the supporting section 82 without being exposed outside.

The backlight power cable 68 is disposed in a gap 93 between an outer wall 89 of the light path 84 in the supporting section 82 and an outer wall of the supporting section 82.

Further, the backlight power cable 68 passes through the gap 93 between the outer wall 89 of the light path 84 and the outer wall of the supporting section 82, and then the backlight power cable 68 is extended, via a rear side of a reflecting face of the prism 88, and connected to the backlight source 90.

Figure 6:
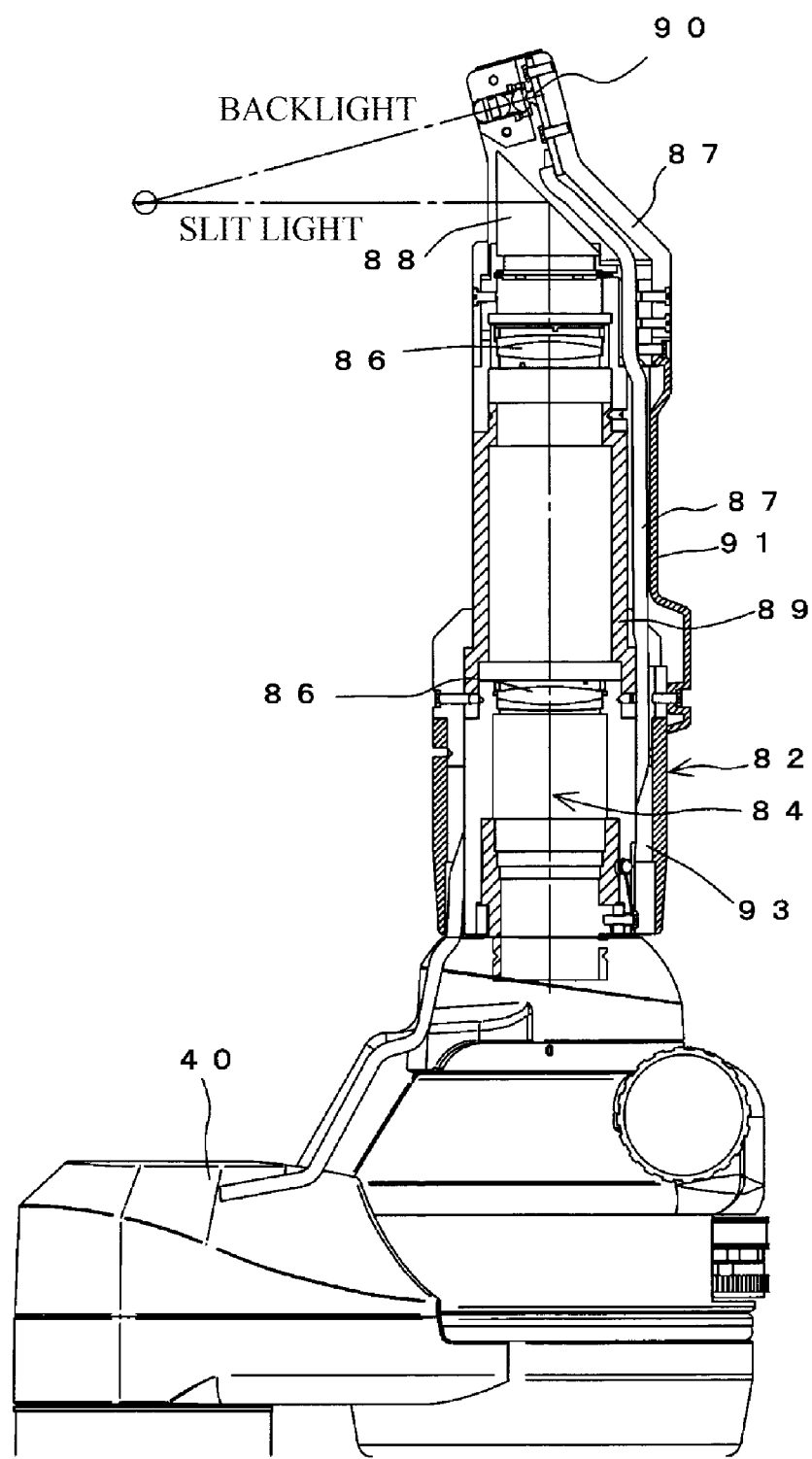
FIG. 6 is a sectional view of the slit lamp microscope of another embodiment.

Note that, the slit lamp is not shown in FIG. 6, but it is provided in the supporting base 40. Further, the slit lamp power cable for supplying electric power to the slit lamp is provided in the supporting baser 40 without being exposed outside.

In each of the above described two embodiments, the mirror unit has the backlight source provided under the reflecting mirror. But, in the present invention, the positional relationship between the reflecting mirror (or the prism) and the backlight source is not limited to that of the above described embodiment.

For example, the reflecting mirror may be a semi-transparent mirror, and the backlight source may be provided in the mirror unit. With this structure, the backlight is emitted in the mirror unit and directed toward the eye of the examinee through the semi-transparent reflecting mirror, and the slit light emitted from above is reflected on the reflecting mirror and directed toward the eye of the examinee.

Further, LEDs are preferable light source as the backlight source, but other light emitting means may be employed.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention has been described in detail, it should be understood that the various changes, substitutions, and alternations could be made hereto without departing from the spirit and scope of the invention.

What is claimed is:
1. A slit lamp microscope, comprising:
a frame;
a supporting base being capable of precisely moving, in a horizontal direction, with respect to the frame;

a supporting section extending upwardly from the supporting base, the supporting section including two connection arms;

a slit light unit attached to a front end part of the supporting section, the slit light unit accommodating a slit lamp for emitting a slit light downward;

a mirror unit being attached to a vertical middle part of the supporting section, the mirror unit having a reflecting mirror for reflecting the slit light emitted from the slit light unit toward an eye of an examinee; and a microscope unit for observing the eye of the examinee, wherein a slit lamp power cable for supplying electric power to the slit lamp and extending from the supporting base, is provided in a hollow part of the supporting section, and the slit lamp power cable is inserted in one of the connection arms of the supporting section and connected to the slit lamp in the slit light unit without being exposed outside.

2. The slit lamp microscope according to claim 1, wherein a backlight source for emitting a backlight, which illuminates a circumference of the slit light toward the eye of the examinee, is provided to the mirror unit, and a backlight power for supplying electric power to the backlight source and extending from the supporting base, is provided in the hollow part formed in the supporting section and connected to the backlight source in the mirror unit without being exposed outside.

3. The slit lamp microscope according to claim 2, wherein the supporting base is disposed such that a clearance is formed between a lower face of the supporting base and an upper face of the frame, a conversion circuit, which converts a commercial electric power source or an electric power source from an AC adapter into a driving power source of the slit lamp and the backlight source, is provided in the inside of the supporting base, and an opening part, into which an electric power cable from the commercial electric power source or the AC adapter is introduced so as to be connected to the conversion circuit, is formed in the lower face of the supporting base.

4. A slit lamp microscope, comprising:

a frame;

a supporting base being capable of precisely moving, in a horizontal direction, with respect to the frame;

a cylindrical supporting section extending upwardly from the supporting base;

a slit light unit provided in the supporting base, the slit light unit emitting a slit light upward through the cylindrical supporting section;

a mirror unit attached to an upper end of the supporting section, the mirror unit having a prism, which reflects the slit light toward an eye of an examinee;

a microscope unit for observing the eye of the examinee; and a backlight source for emitting a backlight, which illuminates a circumference of the slit light, toward the eye of the examinee, the backlight source being provided to the mirror unit, wherein a backlight power cable for supplying electric power to the backlight source extends from the supporting base to inside of the supporting section and is connected to the backlight source in the mirror unit without being exposed outside.

* * * * *